United States Patent [19]

Smith et al.

[11] Patent Number: 5,656,746

[45] Date of Patent: Aug. 12, 1997

[54] TEMPORARY WET STRENGTH POLYMERS FROM OXIDIZED REACTION PRODUCT OF POLYHYDROXY POLYMER AND 1,2-DISUBSTITUTED CARBOXYLIC ALKENE

[75] Inventors: David Jay Smith, Montgomery; Michael Martyn Headlam, Cincinnati, both of Ohio

[73] Assignee: The Proctor & Gamble Company, Cincinnati, Ohio

[21] Appl. No.: 624,764

[22] Filed: Mar. 28, 1996

[51] Int. Cl.$^6$ .............................. C08B 3/00; C07H 11/00
[52] U.S. Cl. .......................... 536/63; 536/115; 536/119; 525/54.21; 525/54.23; 525/54.26; 525/54.3; 525/54.31; 106/208.5
[58] Field of Search ........................ 106/163.1, 164; 525/54.21, 54.23, 54.26, 54.3, 54.31; 536/63, 114, 115, 119; 162/164.7, 175, 176, 177, 178

[56] References Cited

U.S. PATENT DOCUMENTS

| | | | |
|---|---|---|---|
| 3,505,312 | 4/1970 | Malm et al. | 536/32 |
| 3,692,555 | 9/1972 | Aono et al. | 117/33.3 |
| 3,708,305 | 1/1973 | Koyanagi et al. | 96/115 |
| 3,712,886 | 1/1973 | Koyanagi et al. | 536/43 |
| 3,870,702 | 3/1975 | Koyanagi et al. | 536/43 |
| 3,933,746 | 1/1976 | Steele | 536/43 |
| 4,026,928 | 5/1977 | Chaudhary et al. | 562/408 |
| 4,177,073 | 12/1979 | Hata et al. | 430/188 |
| 4,226,981 | 10/1980 | Onda et al. | 536/66 |
| 4,283,553 | 8/1981 | Ivanchev et al. | 560/176 |
| 4,820,307 | 4/1989 | Welch et al. | 8/120 |
| 4,840,875 | 6/1989 | Kunichika et al. | 430/309 |
| 4,939,200 | 7/1990 | Stack et al. | 524/501 |
| 4,983,401 | 1/1991 | Eichel et al. | 424/473 |
| 5,026,559 | 6/1991 | Eichel et al. | 424/458 |
| 5,028,655 | 7/1991 | Stack | 524/522 |
| 5,034,501 | 7/1991 | Ura et al. | 528/263 |
| 5,102,668 | 4/1992 | Eichel et al. | 424/490 |
| 5,104,923 | 4/1992 | Steinwand et al. | 524/461 |
| 5,158,611 | 10/1992 | Ura et al. | 106/499 |
| 5,171,580 | 12/1992 | Iamartino et al. | 424/490 |
| 5,238,686 | 8/1993 | Eichel et al. | 424/461 |

FOREIGN PATENT DOCUMENTS

| | | |
|---|---|---|
| 1115935 | 6/1968 | United Kingdom . |
| 1192797 | 5/1970 | United Kingdom . |

OTHER PUBLICATIONS

JA-7129743-R, published Aug. 30, 1971, Abstract only, Derwent Publications.

J5 4151-906, published Nov. 29, 1979, Abstract only, Derwent Publications.

J6 1094-045-A, published Dec. 5, 1986; Abstract only, Derwent Publications.

JO 1307-743-A, published Dec. 12, 1989; Abstract only, Derwent Publications.

Laguna et al., "Coating II Comparative of Filmogens & Plasticizens on Coating in Rotary Machine", *Ann. Pharm. Francaises*, vol. 32, #12, pp. 641–655 (1974).

Andrews et al., "Efficient Ester Crosslink Finishing For Formaldehyde–free Durable Press Cotton Fabrics", *Am. Dyest. Rep.*, vol. 78, #6, pp. 16,18,23 (1989).

Lenikova et al, "Org. Peroksidy Gomoliticheskie Reakts, Ikh Uchastiem". Rakhimov, A.1, pp. 35–50 (1989).

Brown et al., "Calysis of 1,2,3,4–Butanetetracarboxylic Acid in the Durable Press Finishing of Cotton Textile", *Pap. Int.: Conf. Exhib.*, AATCC, pp. 168–185 (1991).

U.S. application No. 08/624,827 David J. Smith, Jimmie Ed Ruth, Jr., filed on Mar. 28, 1996.

*Primary Examiner*—Nathan M. Nutter
*Attorney, Agent, or Firm*—Loretta J. Henderson; Carl J. Roof; E. Kelly Linman

[57] ABSTRACT

A temporary wet strength polymer and compositions for paper products, e.g., toilet tissue, is disclosed. The temporary wet strength polymer is the oxidation product of an esterified polyhydroxy polymer, more preferably of an esterified polysaccharide. The esterified polymer compound is formed by reacting the polyhydroxy polymer with a 1,2-disubstituted alkene compound that has at least one carboxylic acid group. The temporary wet strength polymer provides paper products having an initial wet strength that enables use of the product in the moistened condition, along with a suitable wet strength decay rate.

30 Claims, No Drawings

TEMPORARY WET STRENGTH POLYMERS FROM OXIDIZED REACTION PRODUCT OF POLYHYDROXY POLYMER AND 1,2-DISUBSTITUTED CARBOXYLIC ALKENE

FIELD OF THE INVENTION

This invention relates to wet strength polymers and compositions which can impart temporary wet strength to paper products, and to paper products having temporary wet strength.

BACKGROUND OF THE INVENTION

Wet strength is a desirable attribute of many disposable paper products that come into contact with water in use, such as napkins, paper towels, household tissues, disposable hospital wear, etc. In particular, it is often desirable that such paper products have sufficient wet strength to enable their use in the moistened or wet condition. Thus, the product should resist tearing, ripping, disintegration and the like such that it substantially maintains its integrity during the intended use. For example, moistened tissue or towel may be used for body or other cleaning. Unfortunately, an untreated cellulose fiber assemblage will typically lose 95% to 97% of its strength when saturated with water such that it cannot usually be used in the moistened or wet condition.

Paper products develop dry strength in part due to interfiber hydrogen bonding. When the paper product is wetted, water disrupts the hydrogen bonds and, as a consequence, lowers the strength of the paper product. Historically, wet strength of paper products has been increased primarily by two approaches. One approach is to prevent water from reaching and disrupting the hydrogen bonds, for example, by coating the paper product. Another approach is to incorporate additives in the paper product which contribute toward the formation of interfiber bonds which are not broken or, for temporary wet strength, which resist being broken, by water. The second approach is commonly the technique of choice, especially for tissue products. In this latter approach, a water soluble wet strength resin may be added to the pulp, generally before the paper product is formed (wet-end addition). The resin generally contains cationic functionalities so that it can be easily retained by the cellulose fibers, which are naturally anionic.

A number of resins have been used or disclosed as being particularly useful for providing wet strength to paper products. Certain of these wet strength additives have resulted in paper products with permanent wet strength, i.e., paper which when placed in an aqueous medium retains a substantial portion of its initial wet strength over time. Exemplary resins of this type include urea-formaldehyde resins, melamine-formaldehyde resins and polyamide-epichlorohydrin resins. Such resins have limited wet strength decay.

Permanent wet strength in paper products is often an unnecessary and undesirable property. Paper products such as toilet tissues, etc., are generally disposed of after brief periods of use into septic systems and the like. Clogging of these systems can result if the paper product permanently retains its hydrolysis-resistant strength properties. Therefore, manufacturers have more recently added temporary wet strength additives to paper products for which wet strength is sufficient for the intended use, but which then decays upon soaking in water. Decay of the wet strength facilitates flow of the paper product through septic systems. Numerous approaches for providing paper products claimed as having good initial wet strength which decays significantly over time have been suggested.

For example, U.S. Pat. No. 3,096,228, Day et at., issued Jul. 2, 1983, U.S. Pat. No. 3,556,932, Coscia et al., issued Jan. 19, 1971; U.S. Pat. No. 3,740,391, Williams et al., issued Jun. 19, 1973; U.S. Pat. No. 4,605,702, Guerro et al., issued Aug. 12, 1986, and U.S. Pat. No. 4,675,394, Solarek et al., issued Jun. 23, 1987, suggest various approaches for achieving temporary wet strength with polymers or other compounds.

While the art has provided a variety of paper products having temporary wet strength, none has provided paper products in the manner of the present invention. It is an object of this invention to provide paper products, including paper tissue products such as toilet tissue, that have an initial wet strength sufficient for use of the paper product in the moistened condition, but which also exhibit wet strength decay (i.e., temporary wet strength) such that very low strength levels are attained subsequent to the period of intended use. Another object of the present invention is to provide paper products having a combination of an initial wet strength sufficient for use of the paper product for body cleaning in the moistened condition, and a rate of wet strength decay sufficient for a flushable product. It is a further object of the present invention to provide tissue paper products having an initial total wet tensile strength of at least about 80 g/inch, preferably at least about 120 g/inch. Yet another object of this invention is to provide tissue paper products having, in addition to these initial total wet strengths, a 30 minute total wet tensile strength of not more than about 40 g/inch, preferably not more than about 20 g/inch. Another object of the invention is to provide tissue paper products having such initial wet strength and which also exhibit a wet strength decay rate after 30 minutes of soaking in neutral pit water of at least about 70%, preferably at least about 80%.

SUMMARY OF THE INVENTION

The present invention relates to temporary wet strength polymers and compositions for paper products, including toilet tissue. The temporary wet strength polymer is formed by oxidizing the reaction product of a polyhydroxy polymer and a 1,2-disubstituted carboxylic alkene to form covalent linkages. The hydroxyl groups of the polymer are reacted with the carboxylic functional group of the alkene to form the covalent linkages. The alkene preferably has at least one other carboxylic functional group such that the alkene is capable of forming an anhydride. The temporary wet strength polymer contains aldehyde groups, which tend to impart temporary wet strength to paper formed with the polymer.

The present invention also relates to paper products, e.g., cellulosic fibrous non-woven webs, e.g., tissue, containing the temporary wet strength polymer. The present invention tends to provide tissue having a high initial wet tensile strength (e.g., at least about 80 g/inch, preferably at least about 120 g/inch), and a suitable 30 minute wet tensile strength. For example, tissue containing the temporary wet strength polymer of the invention may have an initial wet tensile strength of over 120 gram/inch and a 30 minute wet tensile strength of less than 20 gram/inch. Tissue having this initial wet tensile strength can be moistened for use in perianal cleaning without excessive deterioration of the paper tissue during use. The 30 minute wet tensile ensures that the tissue remains flushable with a low risk of clogging.

In a preferred embodiment, at least one component of the paper product has a positive charge to enhance inter-fiber bonding. In alternative embodiments, the positive charge is achieved by forming the temporary wet strength polymer from a polyhydroxy polymer containing cationic groups, or by including a cationic retention aid in the composition.

DETAILED DESCRIPTION OF THE PREFERRED EMBODIMENTS

The temporary wet strength polymer of the present invention can be formed by oxidizing the reaction product of a water-soluble polyhydroxy polymer and a 1,2-disubstituted alkene containing at least one carboxylic functional group capable of reacting with the hydroxyl groups of the polyhydroxy polymer to form covalent linkages (the 1,2-disubstituted alkene is alternatively referred to herein as "carboxylic alkene"). The polyhydroxy polymer that has been reacted with the carboxylic alkene, yet not oxidized, is hereinafter alternatively referred to as "intermediate polymer."

As used herein, "water soluble" includes the ability of a material to be dissolved, dispersed, swollen, hydrated or similarly admixed in water. Similarly, as used herein, reference to the phrase "substantially dissolved," "substantially dissolving" and the like refers to the dissolution, dispersion, swelling, hydration and the like admixture of a material in a liquid medium (e.g., water). The mixture typically forms a generally uniform fluid mixture having, to the naked eye, one physical phase.

The water-soluble, polyhydroxy polymer may be naturally occurring or synthetic. In a preferred embodiment, the polyhydroxy polymer consists essentially of a polysaccharide or a water soluble polysaccharide derivative. Non-limiting examples of suitable polysaccharides are water-soluble cellulosic polymers, including starch; galactomannan polymers, including guar gum and locust bean gum; and water-soluble derivatives thereof. Derivatives include anionic and cationic derivatives of such polysaccharides and ethers and esters of such polysaccharides.

Starches for use herein may suitably be derived from corn, potatoes, tapioca, rice, wheat and the like. Suitable starches may vary over a wide molecular weight range and include dextrins and maltodextrin. Preferred starches are those which do not have a substantial anionic charge, more preferably those which are electronically neutral or cationic, most preferably those which are cationic. The cationic starches typically contain cationic groups such as tetra-alkyl ammonium groups. The cationic groups present in the starch tend to decrease the charge repulsion between the final temporary wet strength polymer and cellulose fibers in order to enhance interfiber bond formation and thus to develop higher initial wet tensile strengths. Exemplary cationic starches include those commercially available from the National Starch and Chemical Corp., New York, N.Y., under the trade names Redibond 5327 and Cato 31.

In general, the initial and 30 minute wet tensile strengths of paper products including a temporary wet strength polymer of the invention tend to increase with an increase in the polymer molecular weight. The molecular weight of the temporary wet strength polymer is determined primarily by the molecular weight of the water-soluble polyhydroxy polymer. Preferred polyhydroxyl polymers of the invention will have a number average molecular weight in the range of from about 3,000 grams/mole (g/mole) to about 1,000,000 g/mole, more preferably in the range of from about 3,000 g/mole to about 10,000 g/mole.

The polyhydroxy polymer is reacted with a 1,2-disubstituted alkene containing at least one carboxylic functional group that is capable of reacting with the hydroxyl groups of the polyhydroxy polymer, to thereby form the intermediate polymer. The carboxylic functional group may be, for example, a carboxylic acid group (—COOH) or an acid amide group (—CONH$_2$), and is preferably a carboxylic acid group. The carboxylic acid group reacts with a hydroxyl group of the polyhydroxy polymer to form an ester linkage, and an amide group may also react with such hydroxyl group to form an ester linkage. The acid amides are far less reactive than the carboxylic acids and are therefore less preferred.

By "1,2-disubstituted," it is meant that each of the doubly bonded carbons is singly bonded to one carbon atom other than the doubly bonded carbon atom, and to a hydrogen atom (—HC=CH—). Without intending to be bound by theory, it is believed that if each doubly bonded carbon atom is not bonded to at least one carbon atom, formaldehyde undesirably tends to form during the oxidation of the intermediate polymer. On the other hand, if more than one carbon atom is bonded to each doubly bonded carbon atom, ketones are undesirably formed when the intermediate polymer is oxidized. The carboxylic alkene may contain one or more carbon-carbon double bonds and may contain other multiple bonds. The alkene will typically contain one carbon-carbon double bond.

The 1,2-disubstituted carbon-carbon double bond is preferably in a cyclic structure. Cyclic alkenes tend to lose fewer aldehyde groups during oxidation of the intermediate polymer, relative to acyclic alkenes. Without intending to be bound by theory, it is believed that the number of aldehyde groups should be maximized in order to maximize the number of hemiacetal and/or N-acylhemiaminal groups if a polyacrylamide is present, in the final paper product, and thus to maximize the initial wet strength of the paper product containing the temporary wet strength polymer of the present invention.

In preferred embodiments, the carboxylic alkene is a polycarboxylic compound that contains at least one additional carboxylic functional group such that the compound is capable of forming an anhydride. Such polycarboxylic compounds tend to more readily react with the hydroxyl groups of the polyhydroxy polymer to form the intermediate polymer such that yields of the temporary wet strength polymer of the present invention are higher than when the carboxylic alkene is not capable of forming an anhydride. As used herein, "anhydride" refers to chemical compounds derived from an acid by the elimination of a molecule of water. The second carboxylic functional group may suitably be a carboxylic acid group or an acid amide group. Thus, the carboxylic alkene may be capable of forming a dicarboxylic acid anhydride or a cyclic imide. It is preferred that each of the carboxylic groups be a carboxylic acid group.

More preferably, the carbon atoms of the carboxylic groups of the polycarboxylic compound are separated by 2–3 carbon atoms in order to facilitate the formation of the anhydride (i.e., the carboxylic groups are positioned 1,2 or 1,3 relative to one another). Most preferably, the carbon atoms of the carboxyl group are separated by 2 carbon atoms since the 1,2 polycarboxylic compounds form anhydrides more readily at lower temperatures than the 1,3 polycarboxylic compounds.

The 1,2-disubstituted alkene group and the carboxylic functional group(s) are preferably unconjugated. Without intending to be bound by theory, it is believed that Michael Addition (1,4) can occur to the alkene bond during the esterification reaction where the alkene group and the carboxylic group(s) are conjugated. This addition reaction would destroy the alkene bond and thus negate aldehyde formation during oxidation of the intermediate polymer.

Preferred carboxylic alkenes are water soluble so as to enable a water-based process.

Suitable carboxylic alkenes include, but are not limited to, cis-1,2,3,6-tetrahydrophthalic acid and 1,2,3,6-tetrahydrophthalamic acid. Derivatives of such compounds, e.g., substituted analogs thereof wherein any of the carbon atoms other than the doubly bonded carbon atoms are mono- or poly- substituted, are also suitable for use herein. A variety of substituent groups may be present. However, the substituent groups should not provide steric hindrance or electronic deactivation of the esterification step such that the rate of esterification is decreased. For reasons of availability and rapid reaction times, the carboxylic alkene is preferably cis-1,2,3,6-tetrahydrophthalic acid.

The intermediate polymer can be formed by a process including the steps of preparing a fluid mixture of the polyhydroxy polymer, the carboxylic alkene, and at least one suitable solvent, heating the mixture to a temperature sufficient to evaporate the solvent and to react the alkene with the polyhydroxy polymer.

The fluid mixture of the polyhydroxy polymer and carboxylic alkene is preferably prepared by mixing a solution of the polymer and a suitable solvent with a solution of the carboxylic alkene and a suitable solvent. The solutions of polymer and the carboxylic alkene are formed by at least substantially dissolving the respective compound in one or more suitable solvents. Alternatively, a single solution can be prepared by substantially dissolving the polymer and carboxylic alkene in one or more solvents. The solvent or mixture thereof is typically selected to provide maximum solubility of the solute(s). Suitable solvents include water, pyridine, or other aprotic solvents. Water is the preferred solvent for both solutes.

The solutions are prepared and combined such that the fluid mixture contains polyhydroxy polymer and carboxylic alkene in an mount to provide a degree of substitution on the polymer molecule of from about 0.25 to about 1.5, more preferably from about 0.5 to about 1.0, most preferably about 1.0. It is typically preferred to maximize the concentration of the solutes in the fluid mixture in order to reduce the time and energy required to evaporate the solvent. Heating can be employed to enhance solubility of the solute in the solvent. For example, the mixture of solute and solvent may be heated to temperatures of up to about 100° C., e.g., from about 70° C. to about 99° C. E.g., at temperatures of at least about 90° C., mixtures of up to about 50 weight % solute in water are suitable.

The solution(s) can be mixed together by any suitable method such as are known in the art. Mixing should be sufficient to ensure substantially uniform reaction between the polysaccharide and the carboxylic alkene.

The fluid mixture is then heated to a temperature and for a time sufficient to substantially remove the solvent from the mixture and to react the polymer hydroxyl groups with the carboxyl group of the alkene to form covalent linkages. Where the preferred carboxylic alkenes, the polycarboxylic compounds, are used, the fluid mixture is heated to a temperature and for a time sufficient to substantially remove the solvent from the mixture, to form the anhydride of the polycarboxylic compound, and to react the anhydride with the hydroxyl groups of the polyhydroxy polymer to form the intermediate polymer (generally by heating to at least 100° C.). The anhydride and intermediate polymer are typically formed by heating the mixture to a temperature in the range of from 120° C.–130° C. for a period of 1–2 hours. The steps of forming the anhydride and the intermediate polymer are preferably performed by heating under vacuum in order to remove any residual solvent and to minimize the presence of oxygen.

In a preferred embodiment, the reaction between the polyhydroxy polymer and the carboxylic alkene is catalyzed by a suitable catalyst. The catalyst tends to result in a faster reaction rate, less decomposition of the polyhydroxy polymer, and a higher yield of the intermediate polymer. Any catalyst such as are known in the art of esterification may be used. A preferred catalyst is sodium hypophosphite ($NaH_2PO_2$), which tends to provide higher yields and less decomposition of the polymer at higher reaction temperatures. The use of sodium hypophosphite as an esterification catalyst has been described, for example, in U.S. Pat. No. 4,820,307, issued to C. M. Welch, incorporated herein by reference. The catalyst is suitably included in the polyhydroxy polymer or carboxylic alkene solution(s).

Where the preferred polysaccharide polymers and 1,2-disubstituted alkenes are used, the resultant ester with a degree of substitution of 1.0 has the following structure:

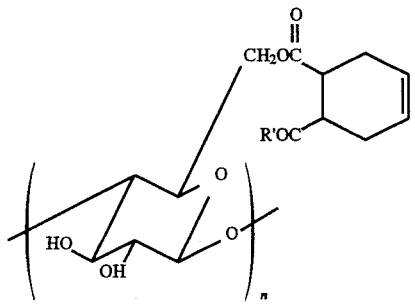

wherein R' is OH or $NH_2$; and n is the degree of polymerization (i.e., DP) of the polysaccharide and is at least one (1), preferably 1–10,000.

As understood in the art, the DP is the inverse of the dextrose equivalent (i.e., DE) of a polysaccharide. Preferably, the DE (or DP) is such that the polysaccharide is soluble in boiling water.

In general, the initial wet tensile strength of the temporary wet strength polymers of the present invention increases with decreasing DE (or increasing DP), while the wet tensile decay rate increases with increasing DE (or decreasing DP). Polysaccharides having a DE of 5 tend to provide a preferred initial wet tensile strength and wet tensile decay rate.

The resultant intermediate polymer is then oxidized to form the temporary wet strength polymer of the present invention. Oxidation is preferably accomplished by forming a fluid mixture of the intermediate polymer in a suitable solvent and introducing a suitable oxidizing agent into the mixture under conditions such that oxidation occurs to form a polymer having aldehyde groups.

The fluid mixture preferably comprises the intermediate polymer substantially dissolved in a suitable solvent. The solvent, temperature of the mixture, and the concentration of the intermediate polymer are preferably selected such that the intermediate polymer and oxidation products thereof are substantially dissolved in the solvent during the oxidation step. Without intending to be limited by theory, it is believed that the oxidizing agent may not efficiently access the intermediate polymer when it is present in solid form, with a resultant reduction in yield of the temporary wet strength polymer. Room temperature (20°–25° C.) is typically sufficient for dissolution.

Water is the preferred solvent for the oxidation reaction. Typically, the fluid mixture contains up to about 10 weight % of the intermediate polymer and at least about 90 weight % water, preferably about 10 weight % intermediate polymer and about 90 weight % water.

The intermediate polymer is preferably converted to salt form to maximize its solubility in water. The salt can be formed by adding a suitable base to the mixture to neutralize the free carboxylic groups which are present in the intermediate polymer. Suitable bases include monovalent metal hydroxides, e.g., NaOH and KOH. Neutralization to a pit of from about 7–8 is preferred. Alkaline pH tends to destroy the aldehyde groups that are formed during the oxidation step. Typically, one equivalent of base per free carboxylic group is added to the mixture.

Suitable oxidizing agents include, for example, ozone and potassium permanganate. Ozone is the preferred oxidation agent for reasons of simplicity, economics, environmental impact, safety, and reaction efficiency.

Ozone oxidation can be accomplished by introducing ozone into the fluid mixture of the intermediate polymer, e.g., by injecting the gas under pressure into the mixture. Although the flow rate and pressure of the ozone may vary over a wide range, exemplary conditions include a flow rate of about 8.0 liters/minute and a flow pressure of about 8 psig. The mixture is preferably cooled to a temperature as low as possible without freezing the mixture (e.g., to temperatures down to about 0° C.) in order to maximize the solubility of the ozone in the mixture. Antifoaming agents such as are known in the art may be added to the mixture to minimize foaming. The oxidation reaction is typically completed by introducing the ozone under the foregoing conditions for a period ranging from 15 to 75 minutes.

The resultant oxidized ester comprises aldehyde groups that can be identified and quantified by known analytical techniques such as NMR. For example, where the preferred polysaccharide polymers and 1,2-disubstituted alkenes are used, the resultant temporary wet strength polymer with a degree of substitution of 1.0 has the following structure:

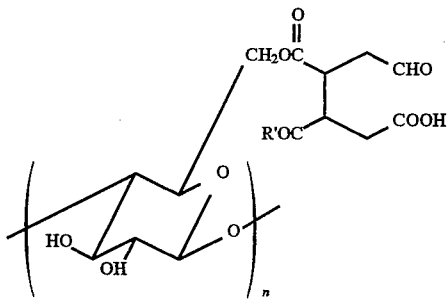

wherein R' and n are as defined above.

The temporary wet strength polymers of the present invention are useful for a wide variety of paper and paper products. As used herein, the terms "paper" and "paper products" include sheet-like masses and molded products containing fibrous cellulosic materials which may be derived from natural sources, such as wood pulp fibers, as well as other fibrous material characterized by having hydroxyl groups attached to the polymer backbone.

Cellulosic fibers of diverse natural origin are applicable to the invention. Digested fibers from softwood (derived from coniferous trees), hardwood (derived from both deciduous trees) or cotton linters are preferably utilized. Fibers from Esparto grass, bagasse, kemp, flax, and other lignaceous and cellulosic fiber sources may also be utilized as raw material in the invention. The optimum cellulosic fiber source utilized in conjunction with this invention will depend upon the particular end use contemplated. Generally wood pulps will be utilized. Applicable wood pulps include chemical pulps, such as Kraft (i.e., sulfate) and sulfite pulps as well as mechanical pulps including, for example, groundwood, thermomechanical pulp (i.e., TMP) and chemithermomechanical pulp (i.e., CTMP). Chemical pulps, however, are preferred since they impart a superior tactile sense of softness to tissue sheets made therefrom. Completely bleached, partially bleached and unbleached fibers are applicable. It may frequently be desired to utilize bleached pulp for its superior brightness and consumer appeal. For products such as paper tissue, paper towels and absorbent pads for diapers, sanitary napkins, catamenials, and other similar absorbent paper products, it is especially preferred to utilize fibers from northern softwood pulp due to its premium strength characteristics.

Also useful in the present invention are fibers derived from recycled paper, which can contain any or all of the above categories as well as other non-fibrous materials such as fillers and adhesives used to facilitate the original paper making.

The paper products may also contain non-cellulosic fibrous polymeric material characterized by having hydroxyl groups attached to the polymer backbone, for example glass fibers and synthetic fibers modified with hydroxyl groups. Other fibrous material, e.g., synthetic fibers, such as rayon, polyethylene and polypropylene fibers, can also be utilized in combination with natural cellulosic fibers or other fibers containing hydroxyl groups. Mixtures of any of the foregoing fibers may be used. Since the strength of the paper product tends to increase with the number of hydroxyl groups in the fibers, it will usually be preferred to employ primarily, more preferably wholly, fibers having hydroxyl groups. Cellulosic fibers are economically preferred.

The temporary wet strength polymers of the present invention are combined with the cellulosic fibers in a manner which allows the polymer and fibers to form a bonded fiber mass, generally in the form of a sheet containing the fibers. The bonded fiber mass has a dry strength and an initial wet strength that is higher than a comparable fiber mass without the polymer.

The paper products are typically formed by a wet laid paper making process. Wet laid paper making processes typically include the steps of providing a slurry containing the cellulosic fibers (the slurry is alternatively referred to herein as a paper making furnish), depositing the slurry of fibers on a substrate such as a foraminous forming wire (e.g., a Fourdrinier wire), and setting the fibers into a sheeted form while the fibers are in a substantially unflocculated condition. The step of setting the fibers into sheeted form may be performed by allowing the fluid to drain and pressing the fibers against the foraminous wire (dewatering), for example, with a screened roll, such as a cylindrical Dandy Roll. Once set, the fibrous sheet may then be dried and optionally compacted as desired.

Treatment of the paper or paper products with the temporary wet strength polymer may involve spraying or printing the cellulosic fibers that have been substantially set in the preparation of the paper product, e.g., by a wet laid process. The set fibers are preferably sprayed or printed with the temporary wet strength polymer in the form of a temporary wet strength composition which comprises a fluid mixture of the polymer substantially dissolved in a suitable solvent. Water is the preferred solvent. The fluid mixture typically contains from about 1–10 weight % of the polymer and about 90–99 weight % of the solvent, for example, a mixture of about 5 weight % of the polymer and about 95 weight % of the solvent, is suitable. In a preferred embodiment, treatment is accomplished by spraying the set fibers.

Alternatively, the temporary wet strength polymer is combined with the cellulosic fibers in the wet-end of a wet laid paper-making process. Thus, the temporary wet strength polymer may suitably be included in the paper-making furnish.

The mount of temporary wet strength polymer that is combined with the cellulosic fibers is generally selected to provide a balance of initial wet strength, wet tensile decay, and optionally other properties, including dry strength, consistent with the objects of the invention. In general, with increasing mounts of the polymer there is an increase in dry strength and initial wet tensile strength and a decrease in the rate of wet strength decay. The paper products will typically contain from about 0.5 to about 5 weight % of the polymer, based on the weight of the cellulosic fibers and optionally other fibers containing hydroxyl groups. Preferably, the paper products will contain from about 0.5 weight % to about 2 weight % of the polymer, based on the weight of such fibers.

The temporary wet strength polymer is allowed to remain in contact with the cellulose fibers for a time and at a temperature sufficient to enable adsorption of the polymer by the fibers and bonding between the polymer and fibers such that significant wet strength is developed via the bond formation (inter-fiber bonds are formed). Bonding may involve ionic bonding and/or covalent bonding. The temporary wet strength polymer is typically readily absorbed by the cellulose fibers where the pH of the temporary wet strength polymer composition is within the range of about 3 to about 8. In general, for a given mount of wet strength polymer (% fiber basis), the initial total wet strength and the 30 minute total wet tensile strength decreases with an increase in pH. Where a cationic starch is used as the polyhydroxy polymer and the wet strength polymer is added at a level of about 1.5–2.0% (fiber basis), a pH of about 8 tends to provide both a relatively high initial total wet strength and a suitable wet strength decay rate over a 30 minute period.

The paper product that is being treated with the temporary wet strength polymer is subjected to a drying step to remove water and any other solvents so as to develop the wet strength. Drying may be accomplished by subjecting the paper product to elevated temperatures, e.g., in the rage of from 85° C.–125° C., for a time sufficient to achieve the desired level of dryness. Typical conditions are a temperature of from 20° C. to about 100° C. and a contact time of from about 60 minutes to about 5 minutes. For example, a period of about 5 minutes at 50° C. provides a product having preferred initial and 30 minute wet tensile values.

Without intending to be bound or otherwise limited by theory, it is believed that the aldehyde groups of the temporary wet strength polymer bond to the cellulosic fibers by formation of hemiacetal and/or N-acylhemiaminal groups through reaction of at least a portion of the cellulosic hydroxyl groups and at least a portion of the aldehyde groups as the paper product dries. The resultant network tends to have a relatively high initial wet tensile strength. The hemiacetal and/or N-acylhemiaminal linkages are reversible in water, slowly reverting to the original temporary wet strength polymer. This reversibility confers temporary wet strength to the paper product. (The reversibility of the hemiaminal groups is typically slower than that of the hemiacetal groups. Therefore, for a maximum rate of wet tensile decay, preferred paper products are those which do not have hemiaminal groups.)

The paper product may further contain conventional paper-making additives such as are known in the art, e.g., retention aids and paper softeners. In a preferred embodiment of the invention, the paper product is treated with a cationic retention aid to decrease the charge repulsion between the temporary wet strength polymer and the cellulose fibers. Fibers treated in this manner tend to have more and stronger interfiber bonds, which serve to provide higher initial wet tensile strengths. The retention aid can be added to the temporary wet strength composition to be applied to the fibers (e.g., as a spray, print mixture, or in the furnish).

Suitable cationic retention aids and their use in paper making applications are well known in the art. Exemplary cationic retention aids include those commercially available as Acco 711 and Cypro 514 (American Cyanamid Corp. of Wayne, N.J.), and Retch 201 (Hercules Inc. of Wilmington, Del.). The retention aid is typically used in an amount of 1–5% based on the weight of the temporary wet strength polymer of this invention.

The present invention is particularly adapted for paper products which are to be disposed into sewer systems, such as toilet tissue. However, it is to be understood that the present invention is applicable to a variety of paper products including, but not limited to disposable absorbent paper products such as those used for household, body, or other cleaning applications and those used for the absorption of body fluids such as urine and menses. Exemplary paper products thus include tissue paper including toilet tissue and facial tissue, paper towels, absorbent materials for diapers, feminine hygiene articles including sanitary napkins, pantiliners and tampons, adult incontinent articles and the like, and writing paper.

With regard to paper tissue, the temporary wet strength polymers of the present invention can be used in any type of tissue paper construction. For example, tissue paper of the present invention can be homogeneous or multi-layered construction; and tissue paper products made therefrom can be of a single-ply or multi-ply construction. The tissue paper preferably has a basis weight of between about 10 g/m$^2$ and about 65 g/m$^2$, and density of about 0.6 g/cm$^3$ or less. More preferably, the basis weight will be about 40 g/m$^2$ or less and the density will be about 0.3 g/cm$^3$ or less. Most preferably, the density will be between about 0.04 g/cm$^3$ and about 0.2 g/cm$^3$. See Column 13, lines 61–67, of U.S. Pat. No. 5,059,282 (Ampulski et al), issued Oct. 22, 1991, which describes how the density of tissue paper is measured. (Unless otherwise specified, all mounts and weights relative to the paper are on a dry basis.) The tissue paper may be conventionally pressed tissue paper, pattern densified tissue paper, and uncompacted, nonpattern-densified tissue paper. These types of tissue paper and methods for making such paper are well known in the art and are described, for example, in U.S. Pat. No. 5,334,286, issued on Aug. 2, 1994 in the names of Dean V. Phan and Paul D. Trekhah, incorporated herein by reference in its entirety.

With respect to paper products that are to be used in the moistened condition, and with particular reference to tissue paper products including toilet paper to be used in the moistened condition for body cleaning or other purposes, it is preferred that the product have an initial wet tensile strength that is high enough for it to withstand the stresses encountered in use. Preferably, the paper product has an initial wet tensile strength of at least about 80 g/inch, more preferably at least about 120 g/inch.

Moreover, it is desirable for tissue paper products to exhibit a wet strength decay rate such that it can be flushed without a significant risk of sewer system clogging. Preferred products have a total wet tensile strength after 30 minutes of soaking in neutral pH water of less than about 40 g/in, preferably less than about 20 g/inch. Flushable paper products may exhibit a wet strength decay rate after 30 minutes of soaking in neutral pH water of at least about 70%, preferably at least about 80%.

In addition, with respect to tissue paper products, and with particular reference to products such as toilet paper, wherein high levels of softness are desired in addition to good initial wet tensile strength with wet strength decay after the period of usage to low strength levels, it is highly preferred for the paper to have an initial total wet tensile strength/total dry tensile strength of at least about 10%, preferably at least about 12%. Lower ratios are less desirable since they tend to be accompanied by a harsh tactile impression. However, paper softening agents may be used to provide greater softness as may be desired.

Paper tissue products formed with the temporary wet strength polymers of the present invention tend to have a high initial total wet tensile strength, a suitable initial total wet strength/dry strength ratio, and a wet strength decay rate suitable for flushability without a significant risk of sewer system clogging under normal use conditions. The aforementioned tensile properties may be determined as described in the following experimental section.

EXPERIMENTAL

Strength Tests

The paper products are aged prior to tensile testing a minimum of 24 hours in a conditioned room where the temperature is 73° F.±4° F. (22.8° C.±2.2° C.) and the relative humidity is 50%±10%.

1. Total Dry Tensile Strength ("TDT")

This test is performed on one inch by five inch (about 2.5 cm×12.7 cm) strips of paper (including creped tissue paper, handsheets, as well as other paper sheets) in a conditioned room where the temperature is 73° F.±4° F. (about 28° C.±2.2° C.) and the relative humidity is 50%±10%. An electronic tensile tester (Model 1122, Instron Corp., Canton, Mass.) is used and operated at a crosshead speed of 2.0 inches per minute (about 1.3 cm per min.) and a gauge length of 4.0 inches (about 10.2.cm). Reference to a machine direction means that the sample being tested is prepared such that the 5" dimension corresponds to that direction. Thus, for a machine direction (MD) TDT, the strips are cut such that the 5" dimension is parallel to the machine direction of manufacture of the paper product. For a cross machine direction (CD) TDT, the strips are cut such that the 5" dimension is parallel to the cross-machine direction of manufacture of the paper product. Machine-direction and cross-machine directions of manufacture are well known terms in the art of paper-making.

The MD and CD tensile strengths are determined using the above equipment and calculations in the conventional manner. The reported value is the arithmetic average of at least eight strips tested for each directional strength. The TDT is the arithmetic total of the MD and CD tensile strengths.

2. Wet Tensile

An electronic tensile tester (Model 1122, Instron Corp.) is used and operated at a crosshead speed of 0.5 inch (about 1.3 cm) per minute and a gauge length of 1.0 inch (about 2.5 cm), using the same size strips as for TDT. The two ends of the strip are placed in the jaws of the machine such and the center of the strip is placed around a stainless steel peg. The strip is soaked in distilled water at about 20° C. for the desired soak time, and then measured for tensile strength. As in the case of the TDT, reference to a machine direction means that the sample being tested is prepared such that the 5" dimension corresponds to that direction.

The MD and CD wet tensile strengths are determined using the above equipment and calculations in the conventional manner. The reported value is the arithmetic average of at least eight strips tested for each directional strength. The total wet tensile strength for a given soak time is the arithmetic total of the MD and CD tensile strengths for that soak time. Initial total wet tensile strength ("ITWT") is measured when the paper has been saturated for 5±0.5 seconds. 30 minute total wet tensile ("30 MTWT") is measured when the paper has been saturated for 30±0.5 minutes.

3. Wet tensile strength decay rate is defined according to the following equation:

$$\% \ Decay = [(ITWT-30MTWT \text{ of paper including the temporary wet strength polymer of the invention}) \times 100]$$

divided by:

(ITWT−30MTWT of comparable paper without any strength additive)

The following non-limiting examples are provided to illustrate the present invention. The scope of the invention is to be determined by the claims which follow.

EXAMPLE I - preparation of temporary wet strength polymer of the present invention 1. preparation of ozone oxidized cis-1,2,3,6-tetrahydrophthalic acid ester of maltodextrin M040 available from Grain Processing Corporation of Musctine, Iowa (DE=5).

A 500 gm quantity of Maltrin M040 (Grain Processing Corp.), 500 gm quantity of cis-1,2,3,6-tetrahydrophthalic acid (THPA), and 30 gm quantity of sodium hypophosphite are stirred and heated in 1.0 liter of distilled water until a homogeneous solution is obtained. The reaction mixture is then placed in a container suitable for efficient evaporation of water from the solution, e.g., Pyrex glass pans. The container is then placed in a Despatch Model LAC1-67-4 forced air oven at 125° C., and the water is evaporated, e.g., by leaving in the oven for about 12–16 hours. The resultant mixture is placed in a vacuum oven at 80°–85° C. for two hours to remove any residual water, then heated at 125°–130° C. for four hours while the esterification proceeds. At the end of this period heating is terminated and the product is allowed to cool to room temperature under vacuum for about 12–16 hours. The resultant product is crushed into a powder, e.g., with mortar and pestle, and suspended with stirring for 30 minutes in 2.0 liters of cold water. The resultant product is separated from the aqueous phase, pressed into a container suitable for efficient evaporation of water from the product, e.g., a Pyrex glass pan, and dried for about 12–16 hours in vacuum oven at 55° C. The resultant maltodextrin ester is powdered in a blender.

A 100 gm batch of the starch ester is prepared by suspending the unpurified powder in 950 ml water and mixing with 20 gm $Na_2CO_3$. This solution is oxidized for 1.5 hours at 8.0 l/min ozone flow, 115 volts, gauge pressure 8 psig using a Polymetrics Model T816 ozone generator with oxygen feed. 1-hexanol is added as needed to control foaming.

2. preparation of ozone oxidized cis-1,2,3,6-tetrahydrophthalic acid (THPA) ester of cationic starch (Redibond 5327 cationic starch from National Starch & Chemical Corp.) is esterified and the resultant ester oxidized as described for the maltodextrin. 30 grams cis.-1,2,3,6-tetrahydrophthalic acid, 120 grams Redibond 5327, 1.8 grams sodium hypophosphite and 210 grams boiling distilled water are mixed to dissolve the solids in the water. The solution is evaporated to dryness by heating at about 105° C. for about 12 hours. The resultant white solid is placed in a vacuum oven at 125° C. for 2 hours. The resultant THPA/cationic starch ester, a yellow solid, is washed with water, filtered and oven dried.

The starch ester is oxidized as follows. 8 grams starch ester, 72 ml water, and 20 ml 1N NaOH are mixed until the ester is dissolved in the liquids. The solution has a pH of 7.18. Hexanol is added to the solution to control foaming. The solution is chilled to about 5° C., then ozone is bubbled into the solution until the color of the solution is bleached (ozone flow rate 2 l/min., oxidation time 25 min.) A small amount of white suspension is seen in the solution. NMR analysis shows the presence of aldehyde peaks and very small alkene peaks.

EXAMPLE II - preparation of paper treated with various wet strength compositions a) creped tissue paper preparation Creped tissue paper treated is made according to the teachings of Sanford and Sisson, U.S. Pat. No. 3,301,746, issued Jan. 31, 1967, and U.S. Pat. No. 3,994,771, Morgan and Rich, issued Nov. 30, 1976. The paper is treated with various wet strength compositions.

The paper machine uses a fixed roof former type of headbox. The fiber furnish comprises 80 weight % eucalyptus and 20 weight % Northern Softwood Kraft fibers formed homogeneously. The headbox dilution water is natural water which is acidified with sulfuric acid to an approximate pH of from about 5.0 to 5.9.

The sheets are formed on a polyester 84M forming wire. This wire is an "84M"; that is, the weave was 84×76 filaments per inch wire woven in a five-shed pattern to form an embryonic web. The embryonic paper web is transferred to a 36×32 five-shed fabric. These patterns and their use are described in Trekban, U.S. Pat. No. 4,191,609, and Trekban, U.S. Pat. No. 4,239,065, both of which are incorporated by reference herein. The embryonic paper sheet is first dried with hot air in a flow-through dryer to a moisture level of about 50% by weight of the sheet. Such a hot air dryer is well known to those skilled in the art. The final drying is accomplished on the surface of a Yankee dryer (to which the web has been adhered with polyvinyl alcohol). The paper is dried to approximately 3% moisture, and then creped from the Yankee with a doctor blade and reeled to provide an ultimate residual crepe of about 20%.

The following solutions are spray applied onto different samples of the above described creped paper at a level of 2 weight % solution on a fiber basis. Spraying is executed with two air atomized nozzles spraying at 30 ml/minute (15 ml/nozzle). Paper consistency at the spray point is 90% and is lowered to 45-47% after spraying. The paper is then redried to 90% consistency. Solutions A-C are representative of the present invention.

(A) Aqueous solution of the ozone oxidized cis-1,2,3,6-tetrahydrophthalic acid ester of maltodextrin M040 made according to Example I, at a solids level of 1.9 weight %. The solution pH is 5.86.

(B) A sample of Solution (A) is titrated with $CaCl_2$ until cloudiness is observed. 25 weight % of the quantity of $CaCl_2$ that produced cloudiness is added and mixed into the above 1.9% solids aqueous Solution (A) on a proportionately scaled up basis. The solution pH is 5.91.

(C) A sample of Solution (A) is titrated with Cypro 514 (a cationic retention aid available from the American Cyanamid Corp. of Wayne, N.J.) until cloudiness is observed. 25 weight % of the quantity of Cypro 514 that produced cloudiness is added and mixed into the above 1.9% solids aqueous Solution (A) on a proportionately scaled up basis. The solution pH is 5.90.

(D) (Comparative) CoBend 1000 (available from National Starch & Chemical Corp. of NY, N.Y.) is cooked in standard preparatory manner by heating in water at pH 2.5 until a solution is attained and diluted with water to a 1.9 weight % solids concentration. The solution pH is 2.83.

The resultant paper products have tensile properties such as reported in Table 1.

TABLE 1

| Wet strength additive | Initial wet tensile, MD | Initial wet tensile, CD | ITWT | 30 minute wet tensile, MD | 30 minute wet tensile, CD | 30 MTWT |
|---|---|---|---|---|---|---|
| A | 144 | 77 | 221 | 18 | 11 | 29 |
| B | 114 | 64 | 178 | 10 | 12 | 22 |
| C | 170 | 94 | 264 | 23 | 23 | 46 |
| D (Comparative) | 314 | 140 | 454 | >187 | 135 | >322 |

Table 1 shows that each of the samples have a high initial total wet tensile strength. Each of the Examples A-C according to the present invention demonstrate significant wet tensile decay. The Comparative Example D has a significantly higher 30 minute total wet tensile strength that is indicative of permanent wet strength.

In an alternative embodiment, paper products are treated in the manner described in reference to Example II (A), but with an aqueous solution of the ozone oxidized cis-1,2,3,6-tetrahydrophthalic acid ester of cationic starch made according to Example I.

The oxidized solution of the THPA/cationic starch ester is spray applied onto different samples of the above described creped paper at a level of 1, 1.5, or 2 weight % solution on a fiber basis. The total solution sprayed in each case is 0.55 grams. The pH of the solution is adjusted prior to spraying. The paper is then air dried to constant weight, cured at 105° C. for 5 minutes, and creped 5 times on a twin roll press.

The resultant paper products have tensile properties such as reported in Table 2.

TABLE 2

| solution pH | polymer % fiber basis | Initial wet tensile, MD | Initial wet tensile, CD | ITWT | 30 minute wet tensile, MD | 30 minute wet tensile, CD | 30 MTWT |
|---|---|---|---|---|---|---|---|
| 4 | 2.0 | 167 | 80 | 247 | 102 | 45 | 147 |
| 6 | 2.0 | 154 | 64 | 218 | 66 | 35 | 101 |
| 8 | 2.0 | 136 | 64 | 200 | 36 | 25 | 61 |
| 4 | 1.0 | 81 | 39 | 120 | 39 | 20 | 59 |
| 6 | 1.0 | 54 | 30 | 84 | — | — | — |
| 8 | 1.0 | 42 | 22 | 164 | — | — | — |
| 8 | 1.5 | 71 | 34 | 105 | 17 | 8 | 25 |

For a given pH, the initial total wet strength and 30 minute total wet strength tends to increase with an increase in the polymer % fiber basis. For a given polymer % fiber basis, the initial total wet strength and 30 minute total wet strength tends to decrease with an increase in pH of the solution being applied. For a polymer % fiber basis of about 1.5–2.0, a pH of about 8 tends to provide an initial total wet strength and a 30 minute total wet strength which are preferred for flushable tissue products.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A temporary wet strength polymer containing aldehyde groups, said polymer prepared by oxidizing the reaction product of (i) a water-soluble polyhydroxy polymer and (ii) a 1,2-disubstituted alkene having a carboxylic functional group capable of reacting with hydroxyl groups of said polyhydroxy polymer, wherein in said reaction product at least a portion of said hydroxyl groups are reacted with said carboxylic functional group of said alkene to form covalent linkages, said reaction product being oxidized to form aldehyde groups.

2. The temporary wet strength polymer of claim 1 wherein said water-soluble polyhydroxy polymer comprises a polysaccharide or a water-soluble derivative thereof.

3. The temporary wet strength polymer of claim 2 wherein said polymer comprises starch or a water-soluble derivative of starch.

4. The temporary wet strength polymer of claim 1 wherein said polyhydroxy polymer comprises cationic groups.

5. The temporary wet strength polymer of claim 1 wherein said alkene is a cyclic alkene.

6. The temporary wet strength polymer of claim 1 wherein said alkene has at least two carboxylic functional groups, said carboxylic functional groups being capable of forming an anhydride.

7. The temporary wet strength polymer of claim 6 wherein said carboxylic functional groups of said alkene are positioned 1,2 or 1,3 relative to one another.

8. The temporary wet strength polymer of claim 7 wherein the 1,2-disubstituted alkene group and said carboxylic functional groups of said alkene are unconjugated.

9. The temporary wet strength polymer claim 6 wherein said carboxylic functional groups are independently selected from the group consisting of carboxylic acid groups and acid amide groups.

10. The temporary wet strength polymer of claim 9 wherein said carboxylic functional groups are carboxylic acid groups.

11. The temporary wet strength polymer of claim 9 wherein said alkene is selected from cis 1,2,3,6 tetrahydrophthalic acid, cis 1,2,3,6-tetrahydrophthalamic acid, and mixtures thereof.

12. The temporary wet strength polymer of claim 1 wherein said reaction product is oxidized with ozone.

13. A temporary wet strength resin composition comprising the temporary wet strength polymer of claim 1.

14. A paper product comprising cellulosic fibers combined with the temporary wet strength resin polymer of claim 1.

15. A temporary wet strength polymer containing aldehyde groups, said polymer comprising the oxidation product of an esterified polyhydroxy polymer, said esterified polyhydroxy polymer comprising a water-soluble polysaccharide or polysaccharide derivative and a 1,2-disubstituted alkene having a carboxylic acid functional group capable of reacting with hydroxyl groups of said polyhydroxy polymer, wherein in said esterified polyhydroxy polymer at least a portion of said hydroxyl groups are reacted with said carboxylic acid group of said alkene to form ester linkages, said esterified polyhydroxy polymer being oxidized to form aldehyde groups.

16. The temporary wet strength polymer of claim 15 wherein said polyhydroxy polymer comprises starch or a water-soluble derivative of starch.

17. The temporary wet strength polymer of claim 15 wherein said polysaccharide or polysaccharide derivative comprises cationic groups.

18. The temporary wet strength polymer of claim 15 wherein said alkene is a cyclic alkene.

19. The temporary wet strength polymer of claim 15 wherein said alkene has a carboxylic functional group capable of forming an anhydride with said carboxylic acid group.

20. The temporary wet strength polymer of claim 19 wherein said carboxylic acid group and said carboxylic functional group are positioned 1,2 or 1,3 relative to one another.

21. The temporary wet strength polymer of claim 20 wherein the 1,2-disubstituted alkene group and said carboxylic groups of said alkene are unconjugated.

22. The temporary wet strength polymer of claim 19 wherein said carboxylic functional group is a carboxylic acid group.

23. A temporary wet strength resin composition comprising the temporary wet strength polymer of claim 15.

24. A paper product comprising cellulosic fibers combined with the temporary wet strength resin polymer of claim 15.

25. A temporary wet strength polymer containing aldehyde groups, said polymer comprising the oxidation product of an esterified polyhydroxy polymer, said esterified polyhydroxy polymer comprising starch or a water-soluble derivative of starch, and a 1,2-disubstituted cyclic alkene having two carboxylic functional groups positioned 1,2 or 1,3 relative to one another, said carboxylic functional groups being selected from the group consisting of carboxylic acid groups and acid amide groups, provided that at least one of said carboxylic functional groups is a carboxylic acid group, the 1,2-disubstituted alkene group and said carboxylic functional groups of said alkene being unconjugated, at least a portion of the hydroxyl groups of said polyhydroxy polymer being reacted with said carboxylic acid group of said alkene to form ester linkages, said esterified polyhydroxy polymer being oxidized to form aldehyde groups.

26. The temporary wet strength polymer of claim 25 wherein said starch or water soluble derivative of starch comprises cationic groups.

27. The temporary wet strength polymer of claim 25 wherein said alkene is selected from cis-1,2,3,6 tetrahydrophthalic acid, cis-1,2,3,6-tetrahydrophthalamic acid, and mixtures thereof.

28. The temporary wet strength polymer of claim 25 wherein said esterified polyhydroxy polymer is oxidized with ozone.

29. A temporary wet strength resin composition comprising the temporary wet strength polymer of claim 25.

30. A paper product comprising cellulosic fibers combined with the temporary wet strength resin polymer of claim 25.

* * * * *

UNITED STATES PATENT AND TRADEMARK OFFICE
CERTIFICATE OF CORRECTION

PATENT NO. : 5,656,746

DATED : August 12, 1997

INVENTOR(S) : D.J. Smith et al.

Page 1 of 2

It is certified that error appears in the above-identified patent and that said Letters Patent is hereby corrected as shown below:

In Col. 2, line 1, "at." should read --al.--.

In Col. 2, line 33, "pit" should read --pH--.

In Col. 4, line 23, "bends" should read --bonds--.

In Col. 5, line 40, "mount" should read --amount--.

In Col. 7, line 11, "pit" should read --pH--.

In Col. 8, line 64, "solvent_" should read --solvent.--.

In Col. 9, line 9, "mount" should read --amount--.

In Col. 9, line 14, "mounts" should read --amounts--.

In Col. 9, line 33, "mount" should read --amount--.

In Col. 9, line 46, "rage" should read --range--.

In Col. 10, line 16, "Retch" should read --Reten--.

In Col. 10, line 47, "mounts" should read --amounts--.

In Col. 10, line 54, "Trekhah" should read --Trokhan--.

In Col. 12, line 66, "cis," should read --cis--.

In Col. 13, line 14, "l/min.," should read --1/min.,--.

In Col. 13, line 45, the first occurrence of "Trekban" should read --Trokhan--.

In Col. 13, line 45), the second occurrence of "Trekban" should read --Trokhan--.

In Col. 14, line 23, "CoBend" should read --CoBond--.

UNITED STATES PATENT AND TRADEMARK OFFICE
CERTIFICATE OF CORRECTION

PATENT NO. : 5,656,746
DATED : August 12, 1997
INVENTOR(S) : D. J. Smith et al.

It is certified that error appears in the above-identified patent and that said Letters Patent is hereby corrected as shown below:

In Col. 15, line 10 of Table 2, under the column headed "ITWT", "164" should read --64--.

Signed and Sealed this

Fourteenth Day of April, 1998

Attest:

BRUCE LEHMAN

Attesting Officer

Commissioner of Patents and Trademarks